United States Patent [19]

Dellinger

[11] 4,396,373
[45] Aug. 2, 1983

[54] MAGNETIC ORTHODONTIC APPLIANCE

[76] Inventor: Eugene L. Dellinger, 1326 Old Lantern Ter., Fort Wayne, Ind. 46825

[21] Appl. No.: 361,032

[22] Filed: Mar. 22, 1982

[51] Int. Cl.³ .............................................. A61C 3/00
[52] U.S. Cl. ........................................ 433/19; 433/6
[58] Field of Search .................. 433/19, 18, 24, 6, 189

[56] References Cited

U.S. PATENT DOCUMENTS

| 3,353,271 | 11/1967 | Blechman | 433/18 |
|---|---|---|---|
| 3,478,742 | 11/1969 | Bohlmann | 433/6 |
| 3,798,770 | 3/1974 | Mitchell | 433/189 |
| 3,984,915 | 10/1976 | Noble et al. | 433/18 |
| 4,017,973 | 4/1977 | Nelson | 433/18 |

Primary Examiner—John J. Wilson
Attorney, Agent, or Firm—George A. Gust

[57] ABSTRACT

This invention relates to an orthodontic appliance for exerting a corrective magnetic force on live teeth in a patient's mouth. The appliance includes two separate rigid caps having internal shapes conforming to the crown portions of juxtaposed teeth in the maxilla and mandible, respectively. The caps are adapted to be removably frictionally secured to such teeth. Two permanent magnets carried by the two caps, respectively, have facing poles which are in registry when the mouth is normally closed and further exert a magnetic force in a direction substantially normal to the occlusal plane. The poles are of extended area such that at least portions thereof remain in juxtaposed registry and the magnetic force maintains substantially in the same direction for normal relative jaw movement.

16 Claims, 9 Drawing Figures

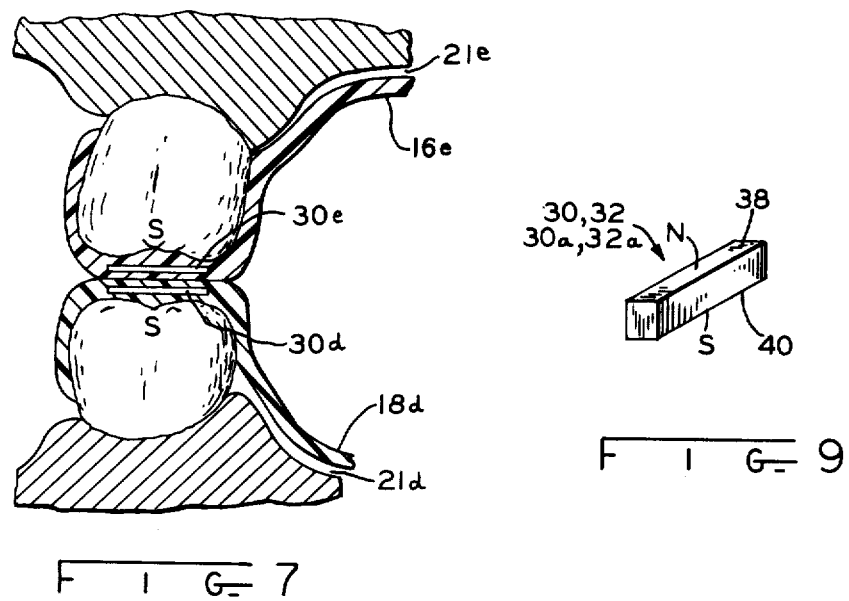
FIG. 7
FIG. 9
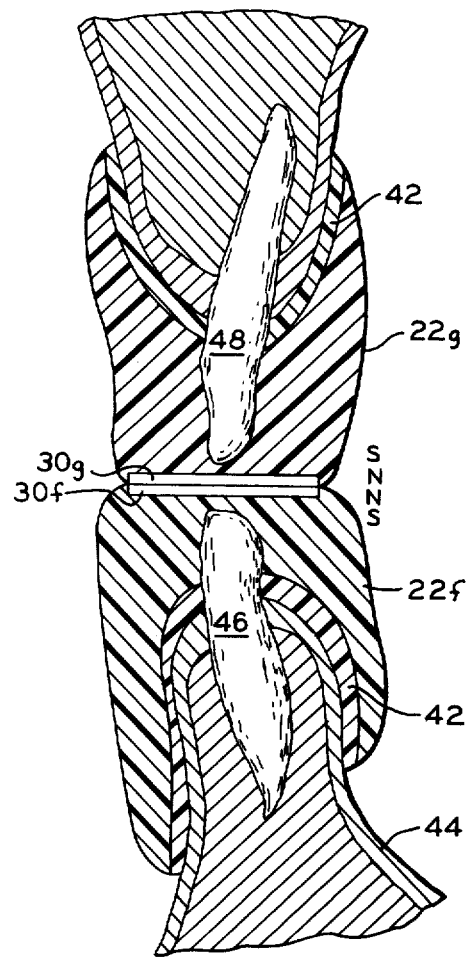
FIG. 8

MAGNETIC ORTHODONTIC APPLIANCE

BACKGROUND OF THE INVENTION

1. Field of the Invention

The present invention relates to orthodontics and more particularly to an appliance which may be removably fitted into place by the wearer and which incorporates permanent magnets for the purpose of generating the desired corrective forces.

2. Description of the Prior Art

Prior to the present invention, many types of appliances incorporating a variety of arrangements of magnetic elements for developing corrective forces have been proposed. Also, magnetic elements have been used in combination with dentures for retaining the latter in the mouth. Representative of this prior art are the following U.S. Pat. Nos. 2,543,773; 2,709,301; 3,353,271; 3,798,770; 3,984,915; 4,017,973 and 4,284,405.

As to those magnetic devices used normally for retaining dentures in position, either magnets are located in the gum with an opposite and attracting magnet in the denture, or like magnets for repulsion are located in the upper and lower dentures. Magnets have also been used to locate dentures in the proper position in the mouth or to hold side-by-side dentures in the correct position. None of these denture arrangements are concerned with the matter of applying corrective forces to live teeth normally treated by an orthodontist.

As to orthodontic appliances, magnets have been attached to teeth by direct bonding, by means of conventional bands and also by means of arch wires. For purposes of this invention, these are regarded as permanent or semi-permanent attachments. Another technique is to employ two juxtaposed magnets, one being mounted on a biting plate and the other on a patient's tooth as disclosed in U.S. Pat. No. 3,984,915. Such magnets in the usual form are elongated with the opposite ends serving as magnetic poles, the pole areas being relatively small. As attached to the teeth, the magnets are usually polarized in end-to-end relation according to the kind of corrective force desired. Further, such magnets are disposed in one of two general arrangements, one in which the magnets interact between teeth in the same dental arch and the other in which they interact between arches. In both, they are permanently affixed as contrasted with being removable by the wearer. In both, the magnetic poles must be rather accurately aligned due to the small pole areas in order to maintain application of the desired corrective force over relatively long periods of time, any misalignment between poles resulting in development of improper forces or of no forces at all. Maintaining alignment as between arches is especially a problem since normal jaw movement causes misalignment of the poles resulting in generation of forces in directions other than that desired.

SUMMARY OF THE INVENTION

The present invention relates to an orthodontic appliance for exerting a corrective force on live teeth which includes two separate permanent magnets disposed on juxtaposed teeth in the upper (maxilla) and lower (mandible) jaws, respectively. Means are provided for securing the two magnets to the teeth, respectively, such magnets having extended area facing poles which are juxtaposed in registry when the jaws are normally closed thereby to exert a magnetic force in a direction substantially normal to the occlusal plane. The pole areas of the magnets further are of such size that at least portions thereof remain juxtaposed to maintain the magnetic force substantially in said direction during normal relative movement between the upper and lower jaws. In one embodiment of this invention, two separate rigid caps are provided with internal shapes conforming to the crown portions of such jaxtaposed teeth. The caps are adapted to be removably frictionally secured to the teeth. The permanent magnets are carried by the caps in such positions as to have facing poles which are in registry.

More specifically, the appliances may include two additional caps and magnets adapted to be affixed in like manner to the counterpart teeth on the opposite sides of the jaws, two frame devices (one upper and one lower) being used for the purpose of rigidly securing the respective caps together. A single magnet may be used in combination with a plurality of teeth in the same arch thereby, for example, to intrude a series of teeth in unison.

In view of the foregoing, it is an object of this invention to provide for improvements in magnetic orthodontic apliances.

The above-mentioned and other features and objects of this invention and the manner of attaining them will become more apparent and the invention itself will be best understood by reference to the following description of an ambodiment of the invention taken in conjunction with the accompanying drawings.

BRIEF DESCRIPTION OF THE DRAWINGS

In the drawings.

FIG. 7 is an enlarged fragmentary section similar to that of FIGS. 4 and 6 but of yet another embodiment;

FIG. 8 is a fragmentary enlarged sectional view of still another embodiment; and FIG. 9 is a perspective view showing a typical magnet which may be employed in the appliance of this invention.

DESCRIPTION

Figure 1:
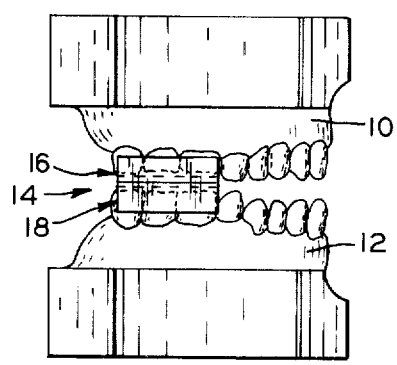
FIG. 1 is a side view of a typical set of maloccluded teeth having one embodiment of the present invention applied thereto.
Figure 2:
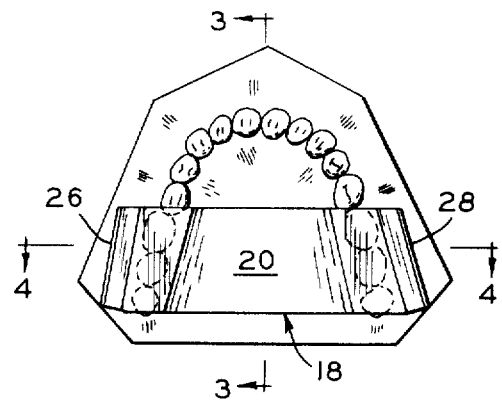
FIG. 2 is a top view of one of the arches with the appliance in position.
Figure 3:
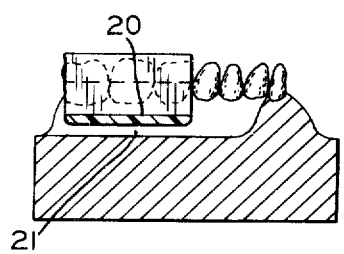
FIG. 3 is a cross section taken substantially along section line 3—3 of FIG. 2.
Figure 4:
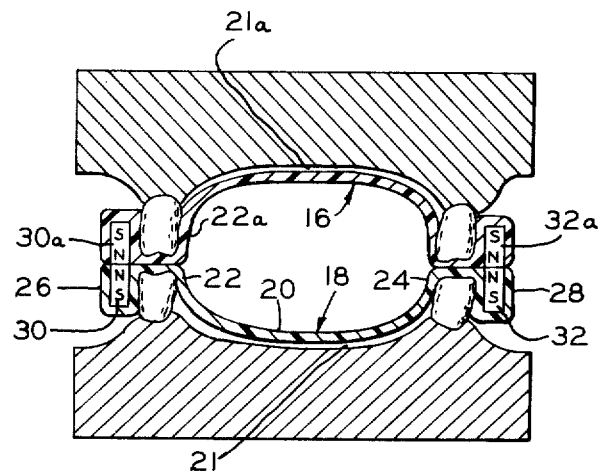
FIG. 4 is a cross section of both dental arches taken substantially along section line 4—4 of FIG. 2.
Figure 5:
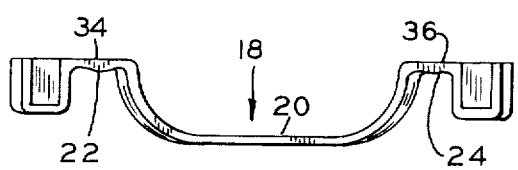
FIG. 5 is an end view of one of the appliances shown in FIGS. 1 and 4.

Referring to the drawings, a typical case of malocclusion is shown in FIG. 1 wherein the maxilla and mandible or jaws 10 and 12 are shown in closed position. As is noted, the anterior teeth are open while the posterior teeth are closed thereby requiring a correction of intruding the posterior teeth in order to provide an occluded bite. An orthodontic appliance in two separable parts or sections is generally indicated by reference numeral 14, the part or section 16 being mounted on the teeth of the upper arch and the part or section 18 on the lower.

As shown more clearly in FIGS. 2 through 5, the sections are constructed essentially alike such that the description of one will suffice for both. Suffix letters are used to distinguish between the features of the top different sections 16, 18.

Generally, each appliance section is of plastic, such as an elongated sheet, formed at the ends to overlie and conform to the crown portions of the three posterior teeth on opposite sides of the jaw, which are to be intruded. The plastic may either be molded to shape to fit the roof or base of the mouth as well as the teeth or alternatively may be vacuum formed. Once formed, the plastic should be relatively hard and somewhat elastic so that it can be removably fitted into place by the wearer.

More particularly, each appliance section has a central band or bridging portion 20 and end caps 22 and 24 which fit over the incisal edges as well as lingual and labial or buccal sides of the particular teeth. The internal shape of the caps should conform to enough of the teeth that it will be retained thereon by reason of frictional engagement with the tooth irregularities. As will become apparent from the description that follows, not much gripping force may be required for certain embodiments of this invention due to the particular placement of the magnetic elements used in conjunction therewith.

Each appliance section 16, 18 is shown as having on the buccal side of the respective caps 22, 24 rectangular retainers 26 and 28 in socket form which are closed on all sides except the one corresponding to the incisal edges of the teeth. These retainers 26, 28 are elongated and of a length corresponding to the width of the bridge 20 and the three teeth to be intruded.

Conforming to and secured within the retainers are elongated permanent magnets 30 and 32, respectively, which are rectangular as more clearly shown in FIG. 9. These magnets may be cemented in place or frictionally secured by the gripping action of the sides of the retainers. The bridging portions 20 of the appliance sections are formed to lie adjacent to but slightly spaced from the roof and base of the mouth (see FIGS. 3, 4 and 6). Also, they may be eliminated entirely provided the caps 22 and 24 extend over a sufficient portion of the respective teeth to be frictionally retained thereby. The upper or incisal portions 34 and 36 of the respective caps 22 and 24 are shown as being flat and form biting edges.

The two appliance sections 16 and 18 are formed as to be juxtaposed so that the respective magnets 30, 30a and 32, 32a are exactly opposite each other when the jaws are normally closed. These magnets are permanent and are polarized through the width dimension with the north pole being on one surface 38 and the opposite pole on the surface 40. The sets of magnets 30, 30a and 32, 32a are oriented with the surfaces 38 thereof lying flat against each other when the jaws are closed to thereby exert repelling forces substantially parallel to the axes of the adjacent teeth. These forces are in a direction to intrude the teeth. With reference to FIG. 1, after a period of time, these repelling, magnetic forces will actually intrude the respective teeth until the dental arches in the two jaws may properly close.

Since the appliance sections 16 and 18 are removably fitted in place, the wearer can remove them from time to time as desired. Fitting is not a problem, since the appliance sections may be fabricated from a laboratory set-up of the teeth, which may then be simply transferred to the patient's mouth by either the patient himself or by the orthodontist. Preferably, the bridges 20 are so formed to provide a slight clearance 21 with the roof and base of the mouth, respectively, to accomodate movement thereof as the teeth intrude. With respect to the lower bridge 20, it may be curved forwardly somewhat along the arch to provide clearance for the tongue.

Figure 6:
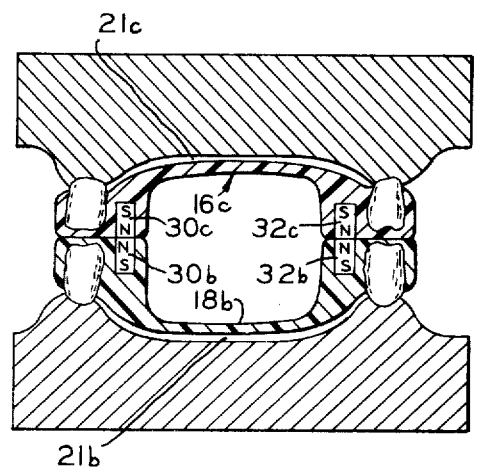
FIG. 6 is a view like FIG. 4 but showing a slightly different embodiment of this invention.

FIGS. 1 through 5 illustrate the magnets being on the labial or buccal sides of the teeth. As shown in FIG. 6, the magnets may be located on the lingual side if preferred. In this figure, like numerals indicate like parts with the suffix letters differing. In both cases, magnets are shown as having pole faces of extended area which congruently engage when the mouth is normally closed.

A slightly different arrangement is shown in FIG. 7 wherein relatively thin, flat magnets 30d and 30e are arranged in parallelism over the facing incisal edges of the teeth being treated. Such magnets are oppositely polarized through the thickness dimensions with the widths and lengths thereof substantially overlying and coinciding with the incisal areas of the respective teeth. Since such magnets are relatively thin, they may be embedded within the plastic of the appliance sections 16e, 18d.

The permanent magnets described thus far may be made of any suitable, permanent magnetic material, including rare earth. Also, magnetic powder in the form of barium ferrite or the like properly polarized may be incorporated within the plastic of the appliance sections 16, 18 such that the plastic itself takes on the character of being magnetized. The fabrication and polarization of such plastic type magnets are well known in the magnet art.

Of particular import is the fact that the juxtaposed magnets in each of the embodiments have facing poles which are of extended area. This area is made large enough so as to accomodate normal lateral jaw movement without the pole faces becoming excessively misaligned. For example, desirably, even though the lower jaw may be moved laterally to its extreme, it is desirable that at least portions of the pole faces remain juxtaposed such that a magnetic repelling force between the two magnets still remains which generally is substantially parallel to the axes of the teeth. Thus, even though the jaws may move while eating or talking, the corrective force will remain applied in the proper direction so as to continuously exert intruding forces on the respective teeth.

In certain instances, it may be desired to cause the portion of the gingiva and bone surrounding the tooth being intruded to also recede. This is accomplished by means of the appliance shown in FIG. 8 where again like numerals indicate like parts. In this embodiment, each of the caps 22f and 22g is provided with a lining 42 which is relatively soft and formed to essentially the shape of the gingiva and bone portion 44. The outer portion of the cap 22f, 22g is of relatively hard plastic material. The lining 42 may be formed of a soft spongy plastic or rubber of such character as will not injure the gingiva. Such lining 42 may be secured in place by means of a suitable adhesive. The remaining portion of the cap is shaped to fit over the tooth as shown. Flat, thin permanent magnets 30f and 30g are embedded in the incisal edge portions of the caps are shown as in the other embodiments. Over a period of time as the two teeth 46 and 48 intrude, the lining portions 42 of the two caps will bear against the surrounding portions of the gingiva and underlying bone causing them to recede.

While the preceding description deals primarily with the correction of multiple projected teeth which are adjacent, individual teeth may likewise be treated by limiting the cap and magnet size to the single juxtaposed teeth in the upper and lower jaws. While such embodiments have been disclosed primarily in connection with the correction of posterior teeth, the appliance sections may also be shaped to conform to the anterior teeth in like manner. Magnets may also be placed on the occlusal surface of the maxilla or mandible. While only the intrusion of teeth has been discussed, it is of course possible to reverse the polarity of one of the magnets in an appliance section 16, 18 in which event the magnets attract. In this event, it is necessary that the caps 22, 24 be firmly attached to the respective teeth in order to avoid separation due to the attractive magnetic force. For teeth which are intruded or impacted, the magnets of course must exert an attractive force and be slightly spaced when the jaws are closed to provide some space within which the teeth may adjust. In order to hold the appliance to the teeth in this instance, it may be desirable to use a suitable cement of the type used for direct bonding of appliances.

While there have been described above the principles of this invention in connection with specific apparatus, it is to be clearly understood that this description is made only by way of example and not as a limitation to the scope of the invention.

What is claimed is:

1. An orthodontic appliance for exerting a corrective magnetic force on live teeth comprising two separate sets of rigid caps having internal shapes conforming to the crown portions of counterpart teeth on the opposite lateral sides of the jaws, said teeth on opposite sides being juxtaposed in the upper and lower jaws, respectively, two separate frame devices rigidly securing said caps of each set together, respectively, one frame device for the upper caps and one for the lower caps, said caps being adapted to be removably secured to such teeth, permanent magnets carried by said upper and lower caps, respectively, and having facing poles which are in registry when said jaws are in occluded position and further exert a magnetic force in a direction substantially normal to the occlusal plane, said poles being of extended area such that at least portions thereof remain in juxtaposed registry and said magnetic force maintains substantially in said direction during normal relative movement of said jaws, said opposite caps and the respective frame device being adapted to hold the teeth covered thereby against lateral movement labially or lingually thereby limiting the magnetic forces exerted by said magnets primarily in directions longitudinally of such teeth.

2. The appliance of claim 1 wherein said magnets are adapted to be disposed on one of the lingual and labial sides of or on the incisal edges of said teeth.

3. The appliance of claim 2 wherein said magnets are elongated to extend between one or more teeth in each jaw.

4. The appliance of claim 1 wherein each frame device and the respective caps are of plastic integrally molded together.

5. The appliance of claim 4 wherein said magnets are elongated and of substantially the same length to extend between two or more teeth in each jaw.

6. The appliance of claim 4 wherein each magnet is at least partially encased in the plastic of the respective cap, and said facing poles are immediately adjacent when the jaws are closed.

7. An orthodontic appliance for exerting a corrective magnetic force on live teeth comprising two separate rigid caps having internal shapes conforming to the crown portions of juxtaposed teeth in the upper and lower jaws, respectively, said caps being adapted to be removably secured to such teeth, two permanent magnets carried by said two caps, respectively, and having facing poles which are in registry when said jaws are in occluded position and further exert a magnetic force in a direction substantially normal to the occlusal plane, said poles being of extended area such that at least portions thereof remain in juxtaposed registry and said magnetic force maintains substantially in said direction during normal relative movement of said jaws, each cap being of a size and shape which fits a portion of the gingiva of the respective tooth, each cap having an exterior of relatively hard material and a relatively soft interior lining in that portion for overlying the gingiva.

8. The appliance of claim 7 wherein the hard material conforms to the portion of the tooth exposed beyond the gingiva and the soft material to the gingiva in the region surrounding the tooth.

9. The appliance of claim 8 wherein said hard and soft materials are of plastic.

10. The appliance of claim 9 wherein said magnets are relatively thin and flat to overlie the incisal edge portions of occluded teeth, said magnets being at least partially embedded within said plastic.

11. The appliance of claim 9 wherein said magnets are adapted to be disposed on one of the labial or lingual sides of said teeth, and are partially embedded within said plastic.

12. The appliance of claim 7 wherein the facing poles are of common polarity whereby corrective intruding forces are exerted on said teeth and the gingiva that surrounds said teeth.

13. An orthodontic appliance for exerting a corrective force on live teeth comprising separate sets of upper and lower permanent magnets adapted to be disposed on juxtaposed teeth in the upper and lower jaws, respectively, on opposite lateral sides of each jaw, means for securing said magnets to said teeth, respectively, first means for rigidly securing the upper magnet on one side of the jaw to the upper magnet on the opposite side, second means for rigidly securing the lower magnet on one side of the jaw to the lower magnet on the opposite side, said first and second securing means comprising bridging portions that extend between the respective magnets and lie adjacent the roof and base of the mouth when the appliance is in use, said magnets having extended area facing poles which are juxtaposed in registry when the jaws are normally closed thereby to exert a magnetic force in a direction substantially parallel to the axes of said teeth, said pole areas of said magnets further being of such size that at least portions thereof remain in juxtaposed registry to maintain said magnetic force substantially in said direction for normal relative movement between said jaws.

14. The appliance of claim 13 where in said magnets are adapted to be disposed on one of the lingual and labial sides or on the incisal edges of said teeth.

15. The appliance of claim 14 wherein said magnets and pole faces are elongated and extend substantially parallel to the occluded jaw plane, said facing poles being of common polarity thereby to exert repelling forces in directions to intrude said teeth.

16. The appliance of claim 14 wherein said first-mentioned means includes carrier devices adapted to be removably frictionally secured to said teeth.

* * * * *